United States Patent

Voigtlander et al.

[11] 3,981,862
[45] Sept. 21, 1976

[54] PREPARATION OF C22-ALKYL DERIVATIVE OF DIGOXIN

[75] Inventors: Wolfgang Voigtlander, Viernheim; Fritz Kaiser, Lampertheim; Wolfgang Schaumann, Heidelberg; Kurt Stach, Mannheim-Waldhof, all of Germany

[73] Assignee: Boehringer Mannheim G.m.b.H., Mannheim, Germany

[22] Filed: Mar. 14, 1975

[21] Appl. No.: 558,381

[30] Foreign Application Priority Data

Apr. 13, 1974  Germany............................ 2418127
July 12, 1974  Germany............................ 2433563
Dec. 4, 1974   Germany............................ 2457219

[52] U.S. Cl..................................... 536/7; 424/182
[51] Int. Cl.².......................................... C07J 19/00
[58] Field of Search..................... 260/210.5, 239.57

[56] References Cited
UNITED STATES PATENTS
3,696,091  10/1972  Eberlein et al. ................. 260/210.5

Primary Examiner—Johnnie R. Brown
Assistant Examiner—Cary Owens
Attorney, Agent, or Firm—Burgess, Dinklage & Sprung

[57] ABSTRACT

A process for the preparation of a C22-alkyl-derivative of digoxin of the formula

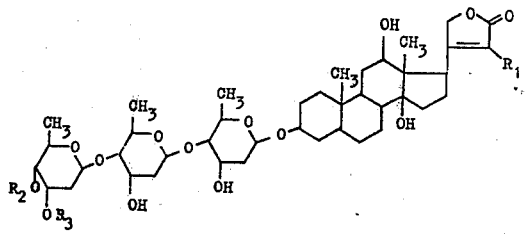

in which
  $R_1$ is an alkyl radical containing up to 4 carbon atoms,
  $R_2$ and $R_3$ are selected from the group consisting of hydrogen, acyl, benzyl, carbobenzoxy, trimethylsilyl, tetrahydropyranyl or phosphonoacyl radicals or together form an alkylidene radical,
comprising reacting a compound of the formula

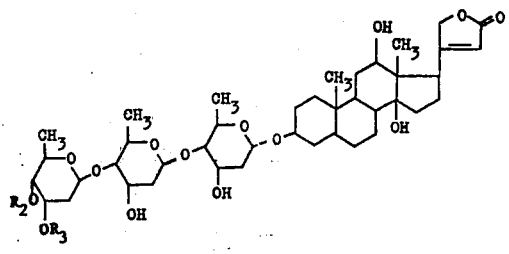

with an alkyl iodide of the formula $R_1I$ in the presence of a strongly polar aprotic solvent and an alkali metal hydride. If $R_2$ and $R_3$ are other than hydrogen they can subsequently be replaced by hydrogen by hydrolysis or hydrogenation. The product can be α- or β-methylated to produce compounds of high resorption and low toxicity.

11 Claims, No Drawings

PREPARATION OF C22-ALKYL DERIVATIVE OF DIGOXIN

The present invention is concerned with a new and improved process for the preparation of digoxin derivatives.

The digoxin derivatives with which the present invention is concerned are compounds of the general formula

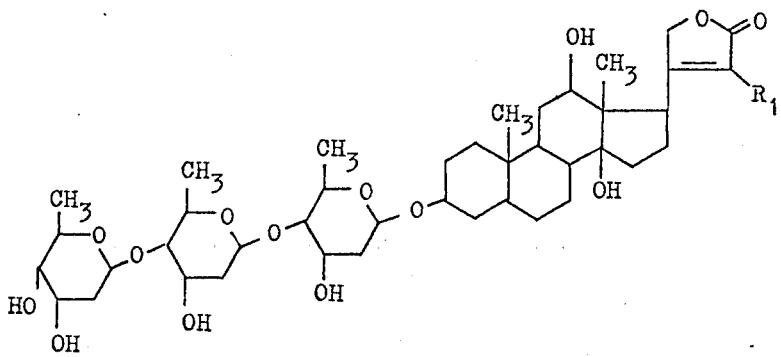

wherein $R_1$ is an alkyl radical containing up to 4 carbon atoms.

German Patent Specification No. 1,929,427 and Chem. Ber., 105, 3686/1972 describe a process according to which the introduction of an alkyl radical on the C22 of the lactone ring of cardenolide glycosides is possible by intramolecular PO-activated cyclization. The products of the process, for example C-22-methyl-digoxin, are, however, obtained via numerous process steps in yields of less than 10% based on the amount of cardenolide glycoside used, for example digoxin.

We have now, surprisingly, found that C22 derivatives of digoxin can be obtained in a simpler manner and in substantially higher yields (about 50%) when digoxin, dissolved in a strongly polar, aprotic solvent, optionally with the temporary protection of the two hydroxyl groups of the terminal digitoxose residue, is reacted with an alkyl iodide in the presence of sodium hydride, whereafter the product of the process is isolated in known manner.

The process according to the present invention is advantageously carried out at ambient temperature, although higher or lower temperatures can be used.

A temporary protection of the hydroxyl groups is preferably carried out by ketalization or by acetalization, i.e. $R_2$ and $R_3$ together are an alkylidene radical preferably of 1 to 4 carbon atoms. However, there can also be used other protective radicals conventionally employed for hydroxyl groups, preferably acyl and especially lower alkanoyl, benzyl, carbobenzoxy, trimethylsilyl, tetrahydropyranyl or phosphonoacyl radicals. The subsequent splitting off of the protective groups can be carried out in known manner by alkaline or acidic hydrolysis or by catalytic hydrogenation.

The strongly polar, aprotic solvent used is preferably dimethyl formamide or dimethyl sulfoxide.

The products of the process can be isolated in known manner, for example by fractionation of the reaction mixture over aluminum oxide and/or by multiplicative partitioning and subsequent crystallization.

The following Examples are given for the purpose of illustrating the present invention:

EXAMPLE 1

C22-Methyl-digoxin

Variant I 10 g of digoxin, dissolved in 100 ml of anhydrous dimethyl sulfoxide, are mixed with 7 ml of methyl iodide. While stirring at ambient temperature, 1.4 g of sodium hydride (50% suspension in mineral oil) is added portionwise within the course of 10 minutes. The reaction mixture is further stirred for 10 minutes, diluted with 400 ml of chloroform and filtered through aluminum oxide. Thereafter the aluminum oxide is washed with chloroform-methanol (1:1 by volume) and filtered and the combined filtrates are evaporated in a vacuum. The crude product thus obtained is subjected to a multiplicative partitioning with the phase mixture chloroform-carbon tetrachloride-methanol-water (1:1:1:1 by volume). The aqueous phase is extracted with chloroform and evaporated in a vacuum. There are obtained 6.5 g of a mixture of digoxin and C22-methyl-digoxin, which is separated by multiplicative partitioning with the phase mixture chloroform-benzene-methanol-water (2:1:2:1 by volume). The organic phase is evaporated and the product obtained is crystallized from chloroform-methanol-ether to give 5.1 g of C22-methyl-digoxin, which has a melting point of 276°–280°C.

Variant II 4 g of isopropylidene-digoxin, dissolved in 40 ml of anhydrous dimethyl formamide, are mixed with 1.4 ml of methyl iodide. While stirring at ambient temperature, 420 mg of sodium hydride (50% suspension in oil) are added thereto incrementally within the course of 15 minutes. The reaction mixture is stirred for a further 5 minutes, diluted with 200 ml of chloroform and filtered through aluminum oxide. Thereafter the aluminum oxide is washed with 200 ml of chloroform-methanol (1:1 by volume), filtered, and the combined filtrates are evaporated in a vacuum. In order to split off the isopropylidene group, the evaporation residue is dissolved in 250 ml of 70% aqueous acetic acid, left to stand for 6 hours at ambient temperature and then diluted with water, whereafter it is extracted with chloroform and the chloroform phase is washed with a 5% solution of sodium bicarbonate in water and evaporated in a vacuum. The crude product is dissolved in chloroform. A pure fraction is obtained by chromatographic separation through a column of aluminum oxide. The pure fraction is evaporated and the residue is crystallized from chloroform-methanol-ether to give 1.95 g of C22-methyl-digoxin, which has a melting point of 275°–279°C.

EXAMPLE 2

C22-Ethyl-digoxin 1.2 g of digoxin, dissolved in 12 ml of anhydrous dimethyl sulfoxide, are mixed with 0.84 ml of ethyl iodide. While stirring at ambient temperature, 170 mg of sodium hydride (50% suspension in oil) are added incrementally, within the course of 10 minutes. The reaction mixture is further stirred for 10 minutes, diluted with 100 ml of chloroform and filtered through aluminum oxide. Thereafter the aluminum oxide is washed with chloroform-methanol (1:1 by volume), filtered and the combined filtrates are evaporated in a vacuum. The crude product thus obtained is dissolved in chloroform and a chromatographic separation is carried out using 50 g of aluminum oxide and chloroform containing variable amounts of methanol as eluent. The fraction containing 10% by volume methanol is evaporated to dryness. The residue is crystallized from chloroform-methanol-ether to give 410 mg of C22-ethyl-digoxin, which has a melting point of 273°–277°C.

Common to the NMR spectra of C22-alkyl-digoxins is the disappearance of the characteristic signal of the proton on C22 ($\delta \approx 5.9$ ppm).

The product is cardioactive but is also especially suited for use in making the further $\alpha$- or $\beta$-methyl derivatives as described in Application Ser. No. 558382 filed Mar. 14, 1975, and now abandoned, filed simultaneously herewith, the disclosure of which is incorporated herein by reference. Such $\alpha$- or $\beta$-methyl derivatives are especially suited for oral administration, as there described, in an amount of about 0.2 to 1 mg per day and are characterized by superior resorption and low toxicity.

It will be appreciated that the instant specification and examples are set forth by way of illustration and not limitation, and that various modifications and changes may be made without departing from the spirit and scope of the present invention.

What is claimed is:
1. A process for the preparation of a C22-alkyl-derivative of digoxin of the formula

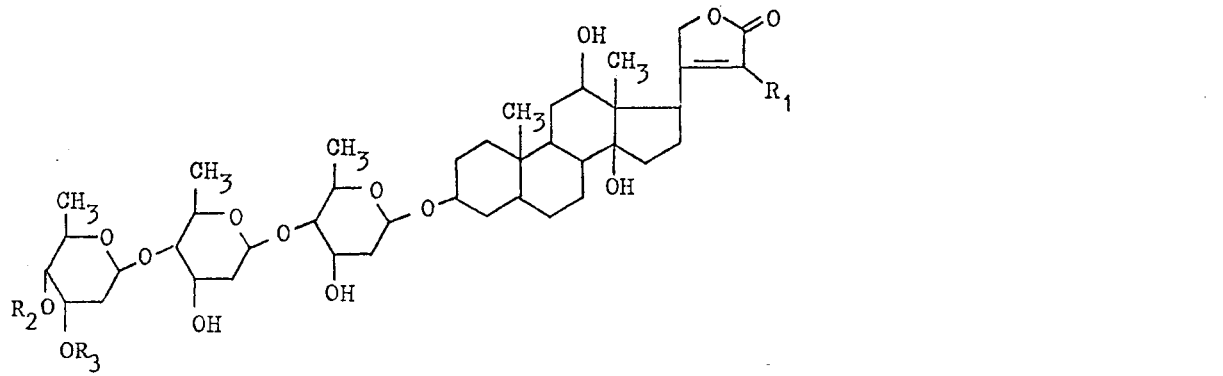

in which
  $R_1$ is alkyl containing up to 4 carbon atoms,
  $R_2$ and $R_3$ are selected from the group consisting of hydrogen, lower alkanoyl, benzyl, carbobenzoxy, trimethylsilyl, tetrahydropyranyl and phosphonic acid or together are alkylidene,
comprising reacting a compound of the formula

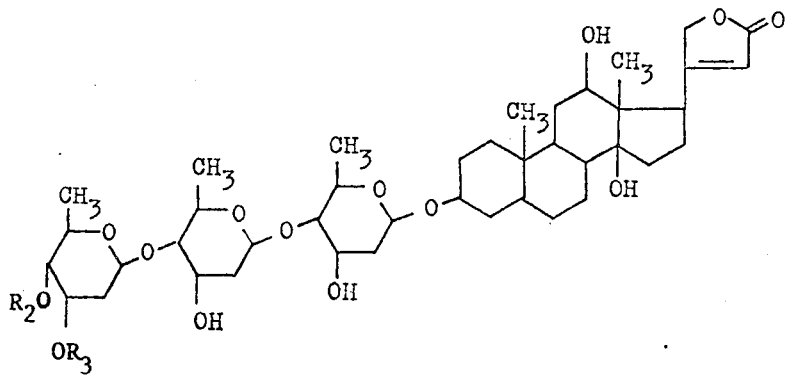

with an alkyl iodide of the formula $R_1I$ in the presence of a strongly polar aprotic solvent and an alkali metal hydride.

2. Process according to claim 1, wherein the reaction is carried out at ambient temperature.

3. Process according to claim 1, wherein $R_2$ and $R_3$ are lower alkanoyl, benzyl, carbobenzoxy, trimethylsilyl, tetrahydropyranyl and phosphonic acid or together are alkylidene, and the reaction product is subsequently hydrolyzed or hydrogenated to replace $R_2$ and $R_3$ by hydrogen.

4. Process according to claim 3, wherein $R_2$ and $R_3$ together are alkylidene and the reaction product is subsequently hydrolyzed.

5. Process according to claim 1, wherein the solvent comprises dimethyl formamide or dimethyl sulfoxide.

6. Process according to claim 1, wherein the reaction mixture is fractionated over aluminum oxide.

7. Process according to claim 1, wherein the reaction product is subjected to multiplicative partitioning and subsequent crystallization.

8. Process according to claim 2, wherein the solvent consists essentially of dimethyl formamide or dimethyl sulfoxide.

9. Process according to claim 8, wherein $R_2$ and $R_3$ together form an alkylidene radical.

10. Process according to claim 8 wherein the reaction solvent comprises dimethyl formamide or dimethyl sulfoxide, the reaction mixture is fractionated over aluminum oxide and the fractionated reaction product is subjected to multiplicative partitioning and subsequent crystallization.

11. Process according to claim 9 wherein the reaction product is subsequently hydrolyzed.

* * * * *